United States Patent
Chen et al.

(10) Patent No.: US 12,258,384 B2
(45) Date of Patent: Mar. 25, 2025

(54) FUSION ALBUMIN NANOPARTICLE AND APPLICATION THEREOF

(71) Applicant: Jiangnan University, Wuxi (CN)

(72) Inventors: Jinghua Chen, Wuxi (CN); Juan Zhou, Wuxi (CN); Mingyu Wang, Wuxi (CN)

(73) Assignee: Jiangnan University, Wuxi (CN)

( * ) Notice: Subject to any disclaimer, the term of this patent is extended or adjusted under 35 U.S.C. 154(b) by 794 days.

(21) Appl. No.: 17/532,182

(22) Filed: Nov. 22, 2021

(65) Prior Publication Data

US 2022/0073590 A1 Mar. 10, 2022

Related U.S. Application Data

(63) Continuation of application No. PCT/CN2019/095707, filed on Jul. 12, 2019.

(30) Foreign Application Priority Data

Jun. 18, 2019 (CN) .......................... 201910525910.4

(51) Int. Cl.
| | | |
|---|---|---|
| C07K 14/765 | (2006.01) |
| A61K 9/16 | (2006.01) |
| A61K 31/337 | (2006.01) |
| A61K 31/704 | (2006.01) |
| A61P 35/00 | (2006.01) |
| A61K 38/00 | (2006.01) |

(52) U.S. Cl.
CPC .......... *C07K 14/765* (2013.01); *A61K 9/1658* (2013.01); *A61K 31/337* (2013.01); *A61K 31/704* (2013.01); *A61P 35/00* (2018.01); *A61K 38/00* (2013.01)

(58) Field of Classification Search
None
See application file for complete search history.

(56) References Cited

U.S. PATENT DOCUMENTS

2018/0162923 A1* 6/2018 Ong ................. C07K 14/70546

FOREIGN PATENT DOCUMENTS

| CN | 103239733 A | 8/2013 |
| CN | 107157950 A | 9/2017 |

* cited by examiner

*Primary Examiner* — Patrick T Lewis
(74) *Attorney, Agent, or Firm* — IPRO, PLLC; Na Xu

(57) ABSTRACT

The disclosure discloses a fusion albumin nanoparticle and application thereof, and belongs to the technical field of biomedicine. In the disclosure, fusion albumin is expressed by using a genetic engineering technology, and the fusion albumin nanoparticle is formed by performing self-assembly and drug loading on the fusion albumin in a neutral aqueous solution. The fusion albumin studied in the disclosure has targetability, pH and enzyme-sensitive functional groups, the nanoparticle prepared by using the fusion albumin has the functions of targetability and controlled drug release, and a method for preparing the fusion albumin nanoparticle is simple and easy to implement and has great application potential.

13 Claims, 8 Drawing Sheets
Specification includes a Sequence Listing.

SEQUENCE LISTING

<160> NUMBER OF SEQ ID NOS: 14

<210> SEQ ID NO 1
<211> LENGTH: 634
<212> TYPE: PRT
<213> ORGANISM: Artificial sequence
<220> FEATURE:
<223> OTHER INFORMATION: Protein translated from synthetic DNA

<400> SEQUENCE: 1

```
Leu Glu Lys Arg Arg Gly Asp Arg Gly Asp Arg Gly Asp Asp Asp Asp
1               5                  10                  15

Asp Lys Asp Ala His Lys Ser Glu Val Ala His Arg Phe Lys Asp Leu
            20                  25                  30

Gly Glu Glu Asn Phe Lys Ala Leu Val Leu Ile Ala Phe Ala Gln Tyr
        35                  40                  45

Leu Gln Gln Cys Pro Phe Glu Asp His Val Lys Leu Val Asn Glu Val
    50                  55                  60

Thr Glu Phe Ala Lys Thr Cys Val Ala Asp Glu Ser Ala Glu Asn Cys
65                  70                  75                  80

Asp Lys Ser Leu His Thr Leu Phe Gly Asp Lys Leu Cys Thr Val Ala
                85                  90                  95

Thr Leu Arg Glu Thr Tyr Gly Glu Met Ala Asp Cys Cys Ala Lys Gln
            100                 105                 110

Glu Pro Glu Arg Asn Glu Cys Phe Leu Gln His Lys Asp Asp Asn Pro
```

```
              115                 120                 125
Asn Leu Pro Arg Leu Val Arg Pro Glu Val Asp Val Met Cys Thr Ala
        130                 135                 140
Phe His Asp Asn Glu Glu Thr Phe Leu Lys Lys Tyr Leu Tyr Glu Ile
145                 150                 155                 160
Ala Arg Arg His Pro Tyr Phe Tyr Ala Pro Glu Leu Leu Phe Phe Ala
                165                 170                 175
Lys Arg Tyr Lys Ala Ala Phe Thr Glu Cys Cys Gln Ala Ala Asp Lys
            180                 185                 190
Ala Ala Cys Leu Leu Pro Lys Leu Asp Glu Leu Arg Asp Glu Gly Lys
        195                 200                 205
Ala Ser Ser Ala Lys Gln Arg Leu Lys Cys Ala Ser Leu Gln Lys Phe
    210                 215                 220
Gly Glu Arg Ala Phe Lys Ala Trp Ala Val Ala Arg Leu Ser Gln Arg
225                 230                 235                 240
Phe Pro Lys Ala Glu Phe Ala Glu Val Ser Lys Leu Val Thr Asp Leu
                245                 250                 255
Thr Lys Val His Thr Glu Cys Cys His Gly Asp Leu Leu Glu Cys Ala
            260                 265                 270
Asp Asp Arg Ala Asp Leu Ala Lys Tyr Ile Cys Glu Asn Gln Asp Ser
        275                 280                 285
Ile Ser Ser Lys Leu Lys Glu Cys Cys Glu Lys Pro Leu Leu Glu Lys
    290                 295                 300
Ser His Cys Ile Ala Glu Val Glu Asn Asp Glu Met Pro Ala Asp Leu
305                 310                 315                 320
Pro Ser Leu Ala Ala Asp Phe Val Glu Ser Lys Asp Val Cys Lys Asn
                325                 330                 335
Tyr Ala Glu Ala Lys Asp Val Phe Leu Gly Met Phe Leu Tyr Glu Tyr
            340                 345                 350
Ala Arg Arg His Pro Asp Tyr Ser Val Val Leu Leu Leu Arg Leu Ala
        355                 360                 365
Lys Thr Tyr Glu Thr Thr Leu Glu Lys Cys Cys Ala Ala Ala Asp Pro
    370                 375                 380
His Glu Cys Tyr Ala Lys Val Phe Asp Glu Phe Lys Pro Leu Val Glu
385                 390                 395                 400
Glu Pro Gln Asn Leu Ile Lys Gln Asn Cys Glu Leu Phe Glu Gln Leu
                405                 410                 415
Gly Glu Tyr Lys Phe Gln Asn Ala Leu Leu Val Arg Tyr Thr Lys Lys
            420                 425                 430
Val Pro Gln Val Ser Thr Pro Thr Leu Val Glu Val Ser Arg Asn Leu
        435                 440                 445
Gly Lys Val Gly Ser Lys Cys Cys Lys His Pro Glu Ala Lys Arg Met
    450                 455                 460
Pro Cys Ala Glu Asp Tyr Leu Ser Val Val Leu Asn Gln Leu Cys Val
465                 470                 475                 480
Leu His Glu Lys Thr Pro Val Ser Asp Arg Val Thr Lys Cys Cys Thr
                485                 490                 495
Glu Ser Leu Val Asn Arg Arg Pro Cys Phe Ser Ala Leu Glu Val Asp
            500                 505                 510
Glu Thr Tyr Val Pro Lys Glu Phe Asn Ala Glu Thr Phe Thr Phe His
        515                 520                 525
Ala Asp Ile Cys Thr Leu Ser Glu Lys Glu Arg Gln Ile Lys Lys Gln
    530                 535                 540
```

Thr Ala Leu Val Glu Leu Val Lys His Lys Pro Lys Ala Thr Lys Glu
545                 550                 555                 560

Gln Leu Lys Ala Val Met Asp Asp Phe Ala Ala Phe Val Glu Lys Cys
                565                 570                 575

Cys Lys Ala Asp Asp Lys Glu Thr Cys Phe Ala Glu Glu Gly Lys Lys
            580                 585                 590

Leu Val Ala Ala Ser Gln Ala Ala Leu Gly Leu Asp Asp Asp Asp Lys
        595                 600                 605

Pro Leu Gly Leu Trp Ala His His His His His His His His His
    610                 615                 620

His His His His His His His His Ala Ala
625                 630

<210> SEQ ID NO 2
<211> LENGTH: 86
<212> TYPE: DNA
<213> ORGANISM: Artificial sequence
<220> FEATURE:
<223> OTHER INFORMATION: Synthetic DNA

<400> SEQUENCE: 2
ccctcgagaa aagacgcgga gatcgcggag atcgcggaga tgatgatgat gataaggatg    60
cacacaagag tgaggttgct catcga                                        86

<210> SEQ ID NO 3
<211> LENGTH: 130
<212> TYPE: DNA
<213> ORGANISM: Artificial sequence
<220> FEATURE:
<223> OTHER INFORMATION: Synthetic DNA

<400> SEQUENCE: 3
ttgcggccgc ttaatggtga tggtgatggt gatggtgatg gtgatggtga tggtgatggt    60
gatggtgtgc ccataatcct aatggcttat catcatcatc taagcctaag gcagcttgac   120
ttgcagcaac                                                         130

<210> SEQ ID NO 4
<211> LENGTH: 86
<212> TYPE: DNA
<213> ORGANISM: Artificial sequence
<220> FEATURE:
<223> OTHER INFORMATION: Synthetic DNA

<400> SEQUENCE: 4
ccctcgagaa aagacgcgga gatcgcggag atcgcggaga tgatgatgat gataaggatg    60
cacacaagag tgaggttgct catcga                                        86

<210> SEQ ID NO 5
<211> LENGTH: 94
<212> TYPE: DNA
<213> ORGANISM: Artificial sequence
<220> FEATURE:
<223> OTHER INFORMATION: Synthetic DNA

<400> SEQUENCE: 5
ttgcggccgc ttaatggtga tggtgatggt gtgcccataa tcctaatggc ttatcatcat    60
catctaagcc taaggcagct tgacttgcag caac                               94

<210> SEQ ID NO 6

```
<211> LENGTH: 90
<212> TYPE: DNA
<213> ORGANISM: Artificial sequence
<220> FEATURE:
<223> OTHER INFORMATION: Synthetic DNA

<400> SEQUENCE: 6
ccctcgagaa aagacgcgga gatcgcggag atcgcggaga tgatgcacac aagagtgagg    60
ttgctcatcg atttaaagat ttgggagaag                                    90

<210> SEQ ID NO 7
<211> LENGTH: 126
<212> TYPE: DNA
<213> ORGANISM: Artificial sequence
<220> FEATURE:
<223> OTHER INFORMATION: Synthetic DNA

<400> SEQUENCE: 7
ttgcggccgc ttaatggtga tggtgatggt gatggtgatg gtgatggtga tggtgatggt    60
gatggtgtgc ccataatcct aatggtaagc ctaaggcagc ttgacttgca gcaacaagtt   120
ttttac                                                             126

<210> SEQ ID NO 8
<211> LENGTH: 86
<212> TYPE: DNA
<213> ORGANISM: Artificial sequence
<220> FEATURE:
<223> OTHER INFORMATION: Synthetic DNA

<400> SEQUENCE: 8
ccctcgagaa aagacgcgga gatcgcggag atcgcggaga tgatgatgat gataaggatg    60
cacacaagag tgaggttgct catcga                                        86

<210> SEQ ID NO 9
<211> LENGTH: 112
<212> TYPE: DNA
<213> ORGANISM: Artificial sequence
<220> FEATURE:
<223> OTHER INFORMATION: Synthetic DNA

<400> SEQUENCE: 9
ttgcggccgc ttaatggtga tggtgatggt gatggtgatg gtgatggtga tggtgatggt    60
gatggtgctt atcatcatca tctaagccta aggcagcttg acttgcagca ac           112

<210> SEQ ID NO 10
<211> LENGTH: 44
<212> TYPE: DNA
<213> ORGANISM: Artificial sequence
<220> FEATURE:
<223> OTHER INFORMATION: Synthetic DNA

<400> SEQUENCE: 10
ccctcgagaa aagagatgca cacaagagtg aggttgctca tcga                    44

<210> SEQ ID NO 11
<211> LENGTH: 130
<212> TYPE: DNA
<213> ORGANISM: Artificial sequence
<220> FEATURE:
<223> OTHER INFORMATION: Synthetic DNA

<400> SEQUENCE: 11
ttgcggccgc ttaatggtga tggtgatggt gatggtgatg gtgatggtga tggtgatggt    60
```

| | |
|---|---|
| gatggtgtgc ccataatcct aatggcttat catcatcatc taagcctaag gcagcttgac | 120 |
| ttgcagcaac | 130 |

<210> SEQ ID NO 12
<211> LENGTH: 44
<212> TYPE: DNA
<213> ORGANISM: Artificial sequence
<220> FEATURE:
<223> OTHER INFORMATION: Synthetic DNA

<400> SEQUENCE: 12

| | |
|---|---|
| ccctcgagaa aagagatgca cacaagagtg aggttgctca tcga | 44 |

<210> SEQ ID NO 13
<211> LENGTH: 112
<212> TYPE: DNA
<213> ORGANISM: Artificial sequence
<220> FEATURE:
<223> OTHER INFORMATION: Synthetic DNA

<400> SEQUENCE: 13

| | |
|---|---|
| ttgcggccgc ttaatggtga tggtgatggt gatggtgatg gtgatggtga tggtgatggt | 60 |
| gatggtgctt atcatcatca tctaagccta aggcagcttg acttgcagca ac | 112 |

<210> SEQ ID NO 14
<211> LENGTH: 5419
<212> TYPE: DNA
<213> ORGANISM: Artificial sequence
<220> FEATURE:
<223> OTHER INFORMATION: Synthetic DNA

<400> SEQUENCE: 14

| | |
|---|---|
| agatctaaca tccaaagacg aaaggttgaa tgaaaccttt ttgccatccg acatccacag | 60 |
| gtccattctc acacataagt gccaaacgca acaggagggg atacactagc agcagaccgt | 120 |
| tgcaaacgca ggacctccac tcctcttctc ctcaacaccc acttttgcca tcgaaaaacc | 180 |
| agcccagtta ttgggcttga ttggagctcg ctcattccaa ttccttctat taggctacta | 240 |
| acaccatgac tttattagcc tgtctatcct ggccccctg gcgaggttca tgtttgttta | 300 |
| tttccgaatg caacaagctc cgcattacac ccgaacatca ctccagatga gggctttctg | 360 |
| agtgtggggt caaatagttt catgttcccc aaatggccca aaactgacag tttaaacgct | 420 |
| gtcttggaac ctaatatgac aaaagcgtga tctcatccaa gatgaactaa gtttggttcg | 480 |
| ttgaaatgct aacggccagt tggtcaaaaa gaaacttcca aaagtcggca taccgtttgt | 540 |
| cttgtttggt attgattgac gaatgctcaa aaataatctc attaatgctt agcgcagtct | 600 |
| ctctatcgct tctgaacccc ggtgcacctg tgccgaaacg caaatgggga aacacccgct | 660 |
| ttttggatga ttatgcattg tctccacatt gtatgcttcc aagattctgg tgggaatact | 720 |
| gctgatagcc taacgttcat gatcaaaatt taactgttct aaccccctact tgacagcaat | 780 |
| atataaacag aaggaagctg ccctgtctta aaccttttt tttatcatca ttattagctt | 840 |
| actttcataa ttgcgactgg ttccaattga caagcttttg attttaacga cttttaacga | 900 |
| caacttgaga agatcaaaaa acaactaatt attcgaaacg atgagatttc cttcaatttt | 960 |
| tactgctgtt ttattcgcag catcctccgc attagctgct ccagtcaaca ctacaacaga | 1020 |
| agatgaaacg gcacaaattc cggctgaagc tgtcatcggt tactcagatt tagaagggga | 1080 |
| tttcgatgtt gctgttttgc catttttccaa cagcacaaat aacgggttat tgtttataaa | 1140 |

```
tactactatt gccagcattg ctgctaaaga agaaggggta tctctcgaga aaagacgcgg    1200
agatcgcgga gatcgcggag atgatgatga tgataaggat gcacacaaga gtgaggttgc    1260
tcatcgattt aaagatttgg gagaagaaaa tttcaaagcc ttggtgttga ttgcctttgc    1320
tcagtatctt cagcagtgtc catttgaaga tcatgtaaaa ttagtgaatg aagtaactga    1380
atttgcaaaa acatgtgttg ctgatgagtc agctgaaaat tgtgacaaat cacttcatac    1440
cctttttgga gacaaattat gcacagtttg aactcttcgt gaaacctatg gtgaaatggc    1500
tgactgctgt gcaaaacaag aacctgagag aaatgaatgc ttcttgcaac acaaagatga    1560
caacccaaac ctcccccgat ggtgagacc agaggttgat gtgatgtgca ctgcttttca    1620
tgacaatgaa gagacatttt tgaaaaaata cttatatgaa attgccagaa gacatcctta    1680
cttttatgcc ccggaactcc ttttctttgc taaaaggtat aaagctgctt ttacagaatg    1740
ttgccaagct gctgataaag ctgcctgcct gttgccaaag ctcgatgaac ttcgggatga    1800
agggaaggct tcgtctgcca aacagagact caagtgtgcc agtctccaaa aatttggaga    1860
aagagctttc aaagcatggg cagtagctcg cctgagccag agatttccca aagctgagtt    1920
tgcagaagtt tccaagttag tgacagatct taccaaagtc cacacggaat gctgccatgg    1980
agatctgctt gaatgtgctg atgacagggc ggaccttgcc aagtatatct gtgaaaatca    2040
agattcgatc tccagtaaac tgaaggaatg ctgtgaaaaa cctctgttgg aaaaatccca    2100
ctgcattgcc gaagtggaaa atgatgagat gcctgctgac ttgccttcat agctgctga    2160 ttttgttgaa agtaaggatg tttgcaaaaa ctatgctgag gcaaaggatg tcttcctggg    2220
catgtttttg tatgaatatg caagaaggca tcctgattac tctgtcgtgc tgctgctgag    2280
acttgccaag acatatgaaa ccactctaga gaagtgctgt gccgctgcag atcctcatga    2340
atgctatgcc aaagtgttcg atgaatttaa acctcttgtg gaagagcctc agaatttaat    2400
caaacaaaat tgtgagcttt ttgagcagct tggagagtac aaattccaga atgcgctatt    2460
agttcgttac accaagaaag taccccaagt gtcaactcca actcttgtag aggtctcaag    2520
aaacctagga aaagtgggca gcaaatgttg taaacatcct gaagcaaaaa gaatgccctg    2580
tgcagaagac tatctatccg tggtcctgaa ccagttatgt gtgttgcatg agaaaacgcc    2640
agtaagtgac agagtcacca aatgctgcac agaatccttg gtgaacaggc gaccatgctt    2700
ttcagctctg gaagtcgatg aaacatacgt tcccaaagag tttaatgctg aaacattcac    2760
cttccatgca gatatatgca cactttctga gaaggagaga caaatcaaga aacaaactgc    2820
acttgttgag ctcgtgaaac acaagcccaa ggcaacaaaa gagcaactga agctgttat    2880 ggatgatttc gcagcttttg tagagaagtg ctgcaaggct gacgataagg agacctgctt    2940
tgccgaggag ggtaaaaaac ttgttgctgc aagtcaagct gccttaggct tagatgatga    3000
tgataagcca ttaggattat gggcacacca tcaccatcac catcaccatc accatcacca    3060
tcaccatcac catcaccatt aagcggccgc cagctttcta gaacaaaaac tcatctcaga    3120
agaggatctg aatagcgccg tcgaccatca tcatcatcat cattgagttt gtagccttag    3180
acatgactgt tcctcagttc aagttgggca cttacgagaa gaccggtctt gctagattct    3240
aatcaagagg atgtcagaat gccatttgcc tgagagatgc aggcttcatt tttgatactt    3300
ttttatttgt aacctatata gtataggatt ttttttgtca ttttgtttct tctcgtacga    3360
gcttgctcct gatcagccta tctcgcagct gatgaatatc ttgtggtagg ggtttgggaa    3420
aatcattcga gtttgatgtt tttcttggta tttcccactc ctcttcagag tacagaagat    3480
taagtgagac cttcgtttgt gcggatcccc cacacaccat agcttcaaaa tgtttctact    3540
```

-continued

```
ccttttttac tcttccagat tttctcggac tccgcgcatc gccgtaccac ttcaaaacac    3600
ccaagcacag catactaaat tttccctctt tcttcctcta gggtgtcgtt aattacccgt    3660
actaaaggtt tggaaaagaa aaaagagacc gcctcgtttc tttttcttcg tcgaaaagg     3720
caataaaaat ttttatcacg tttcttttc ttgaaatttt ttttttagt tttttctct      3780
ttcagtgacc tccattgata tttaagttaa taaacggtct tcaatttctc aagtttcagt   3840
ttcatttttc ttgttctatt acaacttttt ttacttcttg ttcattagaa agaaagcata   3900
gcaatctaat ctaaggggcg gtgttgacaa ttaatcatcg gcatagtata tcggcatagt   3960
ataatacgac aaggtgagga actaaaccat ggccaagttg accagtgccg ttccggtgct   4020
caccgcgcgc gacgtcgccg gagcggtcga gttctggacc gaccggctcg ggttctcccg   4080
ggacttcgtg gaggacgact tcgccggtgt ggtccgggac gacgtgaccc tgttcatcag   4140
cgcggtccag gaccaggtgg tgccggacaa caccctggcc tgggtgtggg tgcgcggcct   4200
ggacgagctg tacgccgagt ggtcggaggt cgtgtccacg aacttccggg acgcctccgg   4260
gccggccatg accgagatcg gcgagcagcc gtggggcgg gagttcgccc tgcgcgaccc    4320
ggccggcaac tgcgtgcact tcgtggccga ggagcaggac tgacacgtcc gacggcggcc   4380
cacgggtccc aggcctcgga gatccgtccc ccttttcctt tgtcgatatc atgtaattag   4440
ttatgtcacg cttacattca cgccctcccc ccacatccgc tctaaccgaa aggaaggag    4500
ttagacaacc tgaagtctag gtccctattt attttttat agttatgtta gtattaagaa    4560
cgttatttat atttcaaatt tttctttttt ttctgtacag acgcgtgtac gcatgtaaca   4620
ttatactgaa aaccttgctt gagaaggttt tgggacgctc gaaggcttta atttgcaagc   4680
tggagaccaa catgtgagca aaaggccagc aaaaggccag gaaccgtaaa aaggccgcgt   4740
tgctggcgtt tttccatagg ctccgccccc ctgacgagca tcacaaaaat cgacgctcaa   4800
gtcagaggtg gcgaaacccg acaggactat aaagatacca ggcgtttccc cctggaagct   4860
ccctcgtgcg ctctcctgtt ccgaccctgc cgcttaccgg atacctgtcc gcctttctcc   4920
cttcgggaag cgtggcgctt tctcaatgct cacgctgtag gtatctcagt tcggtgtagg   4980
tcgttcgctc caagctgggc tgtgtgcacg aaccccccgt tcagcccgac cgctgcgcct   5040
tatccggtaa ctatcgtctt gagtccaacc cggtaagaca cgacttatcg ccactggcag   5100
cagccactgg taacaggatt agcagagcga ggtatgtagg cggtgctaca gagttcttga   5160
agtggtggcc taactacggc tacactagaa ggacagtatt tggtatctgc gctctgctga   5220
agccagttac cttcggaaaa agagttggta gctcttgatc cggcaaacaa accaccgctg   5280
gtagcggtgg tttttttgtt tgcaagcagc agattacgcg cagaaaaaaa ggatctcaag   5340
aagatccttt gatcttttct acggggtctg acgctcagtg gaacgaaaac tcacgttaag   5400
ggatttttggt catgagatc                                               5419
```

FUSION ALBUMIN NANOPARTICLE AND APPLICATION THEREOF

TECHNICAL FIELD

The disclosure relates to a fusion albumin nanoparticle and application thereof, and belongs to the technical field of biomedicine.

BACKGROUND

As an endogenous substance, albumin is a protein without an opsonization effect. It is fund through early researches that the affinity of particles to macrophages can be reduced by coating albumin on a surface of a nanoparticle or a liposome, so that the circulation time is prolonged, and the targetability is improved. In recent years, an albumin nanoparticle drug delivery system with property advantages of a nanoparticle carrier and albumin, has attracted a lot of attention. As a solid sphere formed by using albumin as a carrier to encapsulate or adsorb a drug and then performing curing separation, an albumin nanoparticle has the advantages of good biocompatibility, low toxicity, low irritation, no antigenicity and the like. The drug which can be encapsulated by the albumin nanoparticle includes anti-tumor drugs, anti-tuberculosis drugs, hypoglycemic drugs, antibiotics and the like, and an application of the albumin nanoparticle with a lot of attention at present is using the albumin nanoparticle as a carrier of anti-tumor drugs to improve targetability, reduce toxic side effects and improve a curative effect.

A paclitaxel human serum albumin nanoparticle injection (Abraxane®) developed by AbraxisBioScience Inc of the United States is approved by FDA for marketing and is the first successful case of the albumin nanoparticle drug delivery system. Abraxane® is obtained by combining paclitaxel with human serum albumin. After intravenous injection into human blood circulation, Abraxane® is quickly decomposed into smaller albumin-paclitaxel complexes and then enters tumor cells by using a natural albumin pathway to achieve drug targeting. Abraxane® is mainly obtained by using a unique Nab™ technology (nanoparticle. albuminboundtechnology, Nab™_technology) based on a disulfide bond formation method disclosed by AmericanBioscienceInc. of the United States. The Nab™-technology includes mixing an oil phase containing a water-insoluble drug and an aqueous phase containing albumin to prepare an O/W emulsion under a high shear force (for example, ultrasonic treatment, high pressure homogenization or a similar method) with albumin as a matrix and a stabilizer and then preparing a drug albumin nanoparticle without any conventional surfactant or any polymer core.

However, Abraxane® has some unavoidable problems: first, toxic solvents such as chloroform and dichloromethane need to be used in the Nab™ technology, and a preparation method has the disadvantages of a long preparation period and a cumbersome process; second, access to albumin raw materials is limited by blood sources and extraction pollution, and in the same preparation method, properties of final nano-preparations are affected by batch differences and concentrations of albumin, solvents, temperatures, cross-linking agents and the like; third, since Abraxane® is noncrystalline and amorphous, after intravenous injection into human blood circulation, the nanoparticle is quickly decomposed into smaller albumin-paclitaxel complexes, such that an early drug release risk is unavoidable. In addition, a preparation process of albumin nanoparticles on the market at present is relatively complicated, and nanoparticles with a suitable and uniform particle size are obtained by high-pressure homogenization.

SUMMARY

In order to overcome the defects above in the prior art, a controlled drug release carrier is prepared. The disclosure prepares a controlled drug release type fusion albumin nanoparticle by using a protein recombination technology and provides application of the fusion albumin nanoparticle in preparation of targeted drugs.

The disclosure provides a fusion albumin nanoparticle. The fusion albumin nanoparticle is obtained by sequentially ligating RGD, albumin (HSA), matrix metalloproteinase (MMP) and 6-18 histidines and then performing fusion expression; the RGD, the albumin and the matrix metalloproteinase are ligated by a connecting peptide.

In an example, an amino acid sequence of the connecting peptide is DDDDK.

In an example, a nucleotide sequence encoding the connecting peptide is gatgatgatgataag.

In an example, the albumin is human serum albumin.

In an example, an amino acid sequence of the fusion albumin is as set forth in SEQ ID NO: 1.

The disclosure further provides a gene encoding the fusion albumin.

The disclosure further provides a microbial cell expressing the fusion albumin.

In an example, the cell includes a bacterial cell or a fungal cell.

In an example, the cell is a yeast cell.

In an example, the yeast is *Pichia pastoris* SMD1168H.

In an example, a gene encoding the fusion protein according to claim 1 is fused into a genome of the microbial cell.

The disclosure further provides a method for preparing a controlled drug release type fusion albumin nanocarrier. The method includes ligating the gene encoding the fusion albumin to a carrier and then transforming the gene into a *Pichia pastoris* cell.

In an example, the carrier is pPICZαA.

In an example, a signal peptide α-factor is ligated to the carrier.

In an example, the fusion albumin nanocarrier expresses the fusion albumin as set forth in SEQ ID NO: 1 with *Pichia pastoris* SMD1168H as a host and pPICZαA as a carrier.

In an example, the method includes fermenting the *Pichia pastoris* expressing the fusion albumin, collecting a fermentation solution and extracting a protein.

In an example, the method further includes purifying the extracted protein.

The disclosure further provides a controlled release type pharmaceutical composition, which uses the fusion albumin as a carrier for drug loading.

In an example, a drug is loaded on the fusion albumin by using a pH response self-assembly technology.

In an example, the loaded drug includes but is not limited to paclitaxel, docetaxel and adriamycin.

In an example, the loaded drug further includes siRNA.

In an example, the loading includes mixing the albumin and the drug in a ratio of 1:2 at a pH of 5-6 and then performing self-assembly at a pH adjusted to 7-8.

In an example, the loading includes mixing the albumin and the drug in a ratio of 1:2 at a pH of 5.5 and then adjusting the pH to 7.4.

A sixth objective of the disclosure is to provide a drug loaded by using the controlled drug release type fusion albumin nanocarrier.

The disclosure also claims to protect application of the fusion albumin in preparation of anti-cancer drugs for prevention or treatment of liver cancer, gastric cancer, lung cancer, breast cancer, cervical cancer and the like.

In an example, a drug action object includes but is not limited to cells HepG2, MGC-803, A549, MCF-7 or HeLa.

Beneficial effects: In the disclosure, a series of albumin fusion proteins (RGD-link-HSA-link-MMP-His) are expressed by using a genetic engineering technology, and an albumin fusion protein nanoparticle can be formed by performing self-assembly and drug loading on the fusion albumin. First, by using the protein recombination technology, a cell can be changed into a "factory for mass production of drugs" to ensure safety and reliability of albumin sources; second, the fusion albumin studied in the disclosure has targetability, pH and enzyme-sensitive functional groups, the nanoparticle prepared by using the fusion albumin has the functions of targetability and controlled drug release, and the method for preparing the fusion albumin nanoparticle is simple, easy to implement and suitable for industrial application.

DETAILED DESCRIPTION

A *Pichia pastoris* expression strain SMD1168H and an *Escherichia coli* strain DH5a are preserved in our laboratory.

A YPD liquid (fermentation) culture medium includes 1% (w/w) of yeast powder, 2% (w/w) of peptone and 2% (w/w) of glucose.

A YPD solid (plate) culture medium includes 1% (w/w) of yeast powder, 2% (w/w) of peptone, 2% (w/w) of glucose and 1% (w/w) of agar.

A culture medium BMGY containing an organic carbon source glycerol includes 1%

(w/w) of yeast powder, 2% (w/w) of peptone, 1% (v/v) of glycerol, 100 mmol of a KPB buffer solution (potassium phosphate) and 10% (v/v) of YNB10*.

A culture medium BMMY containing an inorganic carbon source methanol includes 1%

(w/w) of yeast powder, 2% (w/w) of peptone, 0.5% (v/v) of methanol, 100 mmol of a KPB buffer solution (potassium phosphate) and 10% (v/v) of YNB 10*.

An LB liquid culture medium includes 1% (w/w) of peptone, 0.5% (w/w) of yeast powder and 0.5% (w/w) of sodium chloride.

An LB solid culture medium includes 1% (w/w) of peptone, 0.5% (w/w) of yeast powder, 0.5% (w/w) of sodium chloride and 1.5% (w/w) of agar powder.

Example 1 Construction of pPICZαa Recombinant Plasmids

Figure 1A:
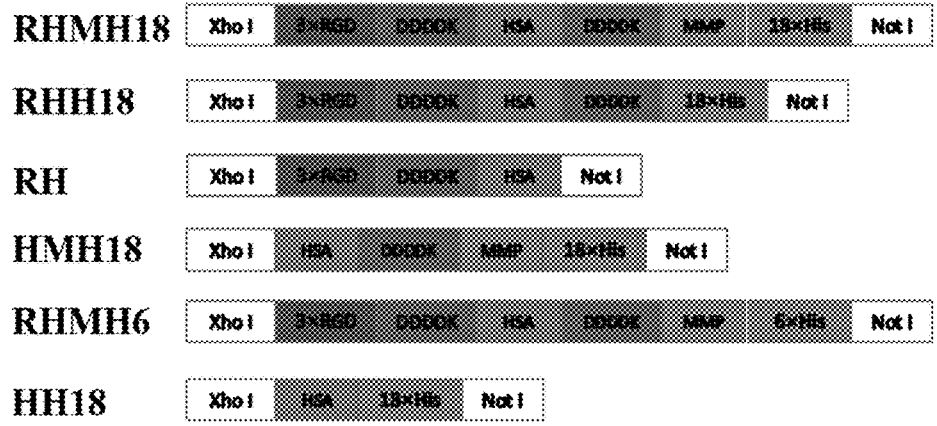
FIG. 1A shows positional relationships and names of components in various fusion gene sequences.

An a secretion signal peptide (α-linker) of *Saccharomyces cerevisiae* was used as a guiding peptide, and a required expression framework was added between XhoI and NotI digestion sites of a pPICZαA/Double linker (an amino acid sequence was gatgatgatgataag) designed as shown in FIG. 1A.

Target genes were obtained by PCR amplification with pPICZαA-HSA (a nucleotide sequence was as set forth in SEQ ID NO: 14) as a template and primers in Table 1. After PCR amplification, gene fragments such as 3RGD-link-HSA-link-MMP-18His, 3RGD-link-HSA-link-MMP-6His, 3RGD-HSA, 3RGD-link-HSA-link-18His, HSA-link-MMP-18His and HSA-18His were separately obtained, the primers used in PCR were shown in Table 1, and underlined gene sequences were sequences at digestion sites. Reaction conditions were shown in Table 2.

TABLE 1

Target gene amplification primer list

| Primer name | Primer sequence |
|---|---|
| 3RGD-link-HSA-link-MMP-18His (RHMH18) | 5'-ccctcgagaaaagaCGCGGAGATCGCGGAGATCGCGGAGATGATGATGATAAGGATGCACACAAGAGTGAGGTTGCTCATCGA-3' (SEQ ID NO: 2)<br>5'-ttgcggccgcTTAATGGTGATGGTGATGGTGATGGTGATGGTGATGGTGATGGTGATGGTGTGCCCATAATCCTAATGGCTTATCATCATCATCTAAGCCTAAGGCAGCTTGACTTGCAGCAAC-3' (SEQ ID NO: 3) |
| 3RGD-link-HSA- | 5'- |

TABLE 1-continued

Target gene amplification primer list

| Primer name | Primer sequence |
|---|---|
| link-MMP-6His (RHMH6) | 5'-ccctcgagaaaagaCGCGGAGATCGCGGAGATCGCGGAGATG ATGATGATGATAAGGATGCACACAAGAGTGAGGTTGCTCAT CGA-3' (SEQ ID NO: 4)<br>5'-ttgcggccgcTTAATGGTGATGGTGATGGTGTGCCCATAATCCT AATGGCTTATCATCATCATCTAAGCCTAAGGCAGCTTGACTT GCAGCAAC-3' (SEQ ID NO: 5) |
| 3RGD-HSA (RH) | 5'-ccctcgagaaaagaCGCGGAGATCGCGGAGATCGCGGAGATG ATGCACACAAGAGTGAGGTTGCTCATCGATTTAAAGATTTG GGAGAAG-3' (SEQ ID NO: 6)<br>5'-ttgcggccgcTTAATGGTGATGGTGATGGTGATGGTGATGGTG ATGGTGATGGTGATGGTGATGTGTGCCCATAATCCTAATGG TAAGCCTAAGGCAGCTTGACTTGCAGCAACAAGTTTTTTAC-3' (SEQ ID NO: 7) |
| 3RGD-link-HSA-link-18His (RHH18) | 5'-ccctcgagaaaagaCGCGGAGATCGCGGAGATCGCGGAGATG ATGATGATGATAAGGATGCACACAAGAGTGAGGTTGCTCAT CGA-3' (SEQ ID NO: 8)<br>5'-ttgcggccgcTTAATGGTGATGGTGATGGTGATGGTGATGGTG ATGGTGATGGTGATGGTGATGGTGCTTATCATCATCATCTAA GCCTAAGGCAGCTTGACTTGCAGCAAC-3' (SEQ ID NO: 9) |
| HSA-link-MMP-18His (HMH18) | 5'-ccctcgagaaaagaGATGCACACAAGAGTGAGGTTGCTCATCG A-3' (SEQ ID NO: 10)<br>5'-ttgcggccgcTTAATGGTGATGGTGATGGTGATGGTGATGGTG ATGGTGATGGTGATGGTGATGTGTGCCCATAATCCTAATGG CTTATCATCATCATCTAAGCCTAAGGCAGCTTGACTTGCAGC AAC-3' (SEQ ID NO: 11) |
| HSA-18His (HH18) | 5'-ccctcgagaaaagaGATGCACACAAGAGTGAGGTTGCTCATCG A-3' (SEQ ID NO: 12)<br>5'-ttgcggccgcTTAATGGTGATGGTGATGGTGATGGTGATGGTG ATGGTGATGGTGATGGTGATGGTGCTTATCATCATCATCTAA GCCTAAGGCAGCTTGACTTGCAGCAAC-3' (SEQ ID NO: 13) |

TABLE 2

PCR amplification systems and conditions

Reaction system

| Reagent | Volume (μL) |
|---|---|
| ddH₂O | 30 |
| Primes Star Max (2X) | 20 |
| Upstream primer | 1 |
| Downstream primer | 1 |
| pPICZαA-HSA | 2 |

Reaction condition

| | | |
|---|---|---|
| Predenaturation | 95° C. | 4 min |
| Denaturation | 95° C. | 30 s |
| Annealing | 55° C. | 45 s |
| Extension | 72° C. | 90 s |
| Circulation for 30 times | | |
| Full extension | 72° C. | 10 min |

A target fragment was obtained by separating a series of obtained gene fragments with nucleic acid gel electrophoresis and then recovered with a column DNA gel kit, and a recovered DNA fragment was subjected to double digestion in a metal bath at 37° C. for 30 minutes and then purified by using a column PCR product purification kit. At the same time, a pPICZαA plasmid preserved in a laboratory was subjected to double digestion in a metal bath at 37° C. for 2 hours, and a plasmid fragment was obtained by nucleic acid gel electrophoresis and then recovered with a column DNA gel recovery kit. Digestion systems were shown in Table 3.

TABLE 3

Digestion systems of a target gene and a vector

| Digestion system of the target gene | | Digestion system of the vector | |
|---|---|---|---|
| Reagent | Volume (μL) | Reagent | Volume (μL) |
| Target fragment | 1 | pPICZα A | 4 |
| Xho I | 1 | Xho I | 1 |
| Not I | 1 | Not I | 1 |
| Buffer | 3 | Buffer | 6 |
| ddH₂O | 10 | ddH₂O | 38 |

The obtained plasmid fragment was ligated to the target gene fragment in a metal bath at 22° C. for 1 hour, and a ligation system was shown in Table 4.

TABLE 4

Ligation system of the target gene and
the vector after digestion

| Reagent | Volume (μL) |
|---|---|
| pPICZα A | 1 |
| Target gene | 7 |
| T4 ligase | 1 |
| Buffer | 1 |

Figure 1B:
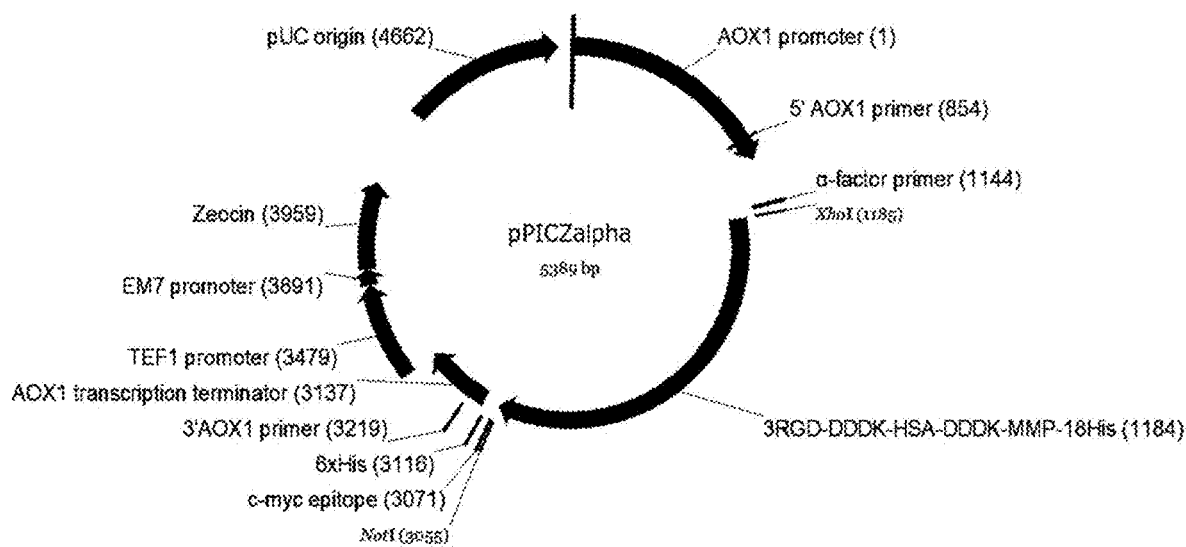
FIG. 1B is a schematic diagram of a constructed pPICZαA-RGD-HSA-MMP-His vector, where a target gene is inserted between Xho I and Not I.
Figure 1C:
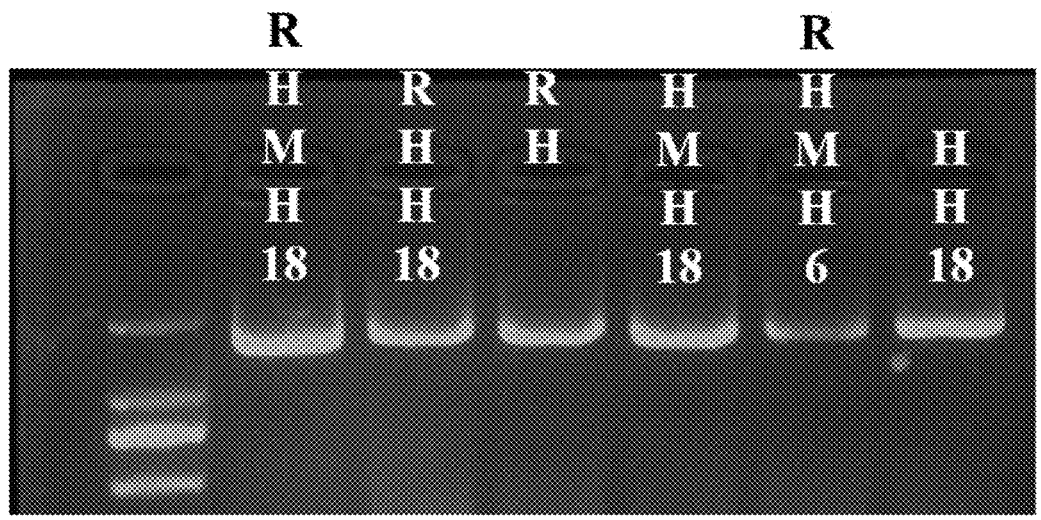
FIG. 1C is a nucleic acid gel electrophoresis diagram of various gene sequences amplified after fusion PCR.
Figure 1D:
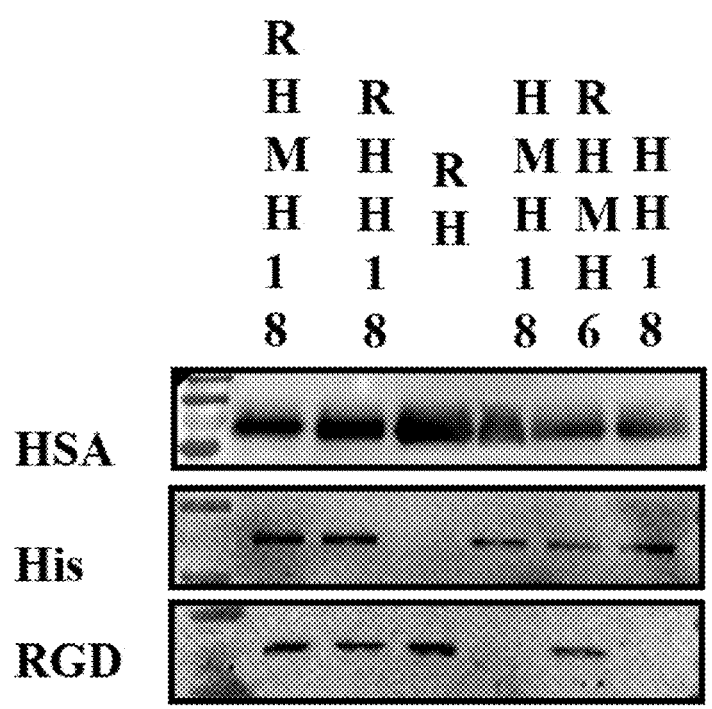
FIG. 1D shows Western Blot analysis results of various albumin fusion proteins, including HSA, His and RGD specific analysis from top to bottom.

The ligated plasmid with the target gene was transformed into DH5a and then cultured in a non-resistant LB culture medium (500 μL) at 37° C. and a shaker speed of 200 rpm for 1 hour, 100 μL of the plasmid was spread on a Zeocin-resistant LB solid culture medium with a concentration of 25 μg/mL and then cultured overnight, a single colony was selected, and a positive plasmid obtained by screening was subjected to double digestion verification, PCR verification and sequencing verification. As shown in FIG. 1B, a constructed recombinant expression plasmid was an expected plasmid. The recombinant plasmid was sent to a third-party sequencing company for sequencing and sequence comparison by using professional software, and it was shown that a successful sequencing result was completely consistent with an expected gene sequence, indicating that the recombinant plasmid pPICZαA-3RGD-link-HSA-link-MMP-18His was successfully constructed.

Recombinant plasmids pPICZαA-3RGD-link-HSA-link-MMP-6His, pPICZαA-3RGD-HSA, pPICZαA 3RGD-link-HSA-link-18His, pPICZαA-HSA-link-MMP-18His and pPICZαA-HSA-18His were constructed by using the same method.

Example 2 Construction and Screening of Recombinant Strains

The recombinant plasmid pPICZαA-18His-HSA-MMP-RGD constructed in Example 1 was subjected to linearized digestion with Sal I and mixed electric shock (1.5 kV, 40 μF, 160 Ω) with competent cells of SMD1168H for transformation. The competent cells of Pichia pastoris SMD1168 were prepared by using a standard method. An obtained mixture was cultured on a YPD plate for four days. Positively cloned strains were selected and subjected to colony PCR verification. Recombinant strains expressing proteins RHMH18, RHMH6, RHH18, RH, HMH18 and HH18 were separately obtained. Ten positively cloned strains with obvious colonies were separately selected and cultured in a YPD liquid culture medium for three days. Supernatants were collected, protein contents of fusion proteins (RHMH18, RHMH6, RHH18, RH, HMH18 and HH18) in the supernatants were detected by using a urine microalbumin detection kit, and a cloned strain with high expression was selected.

Figure 1E:
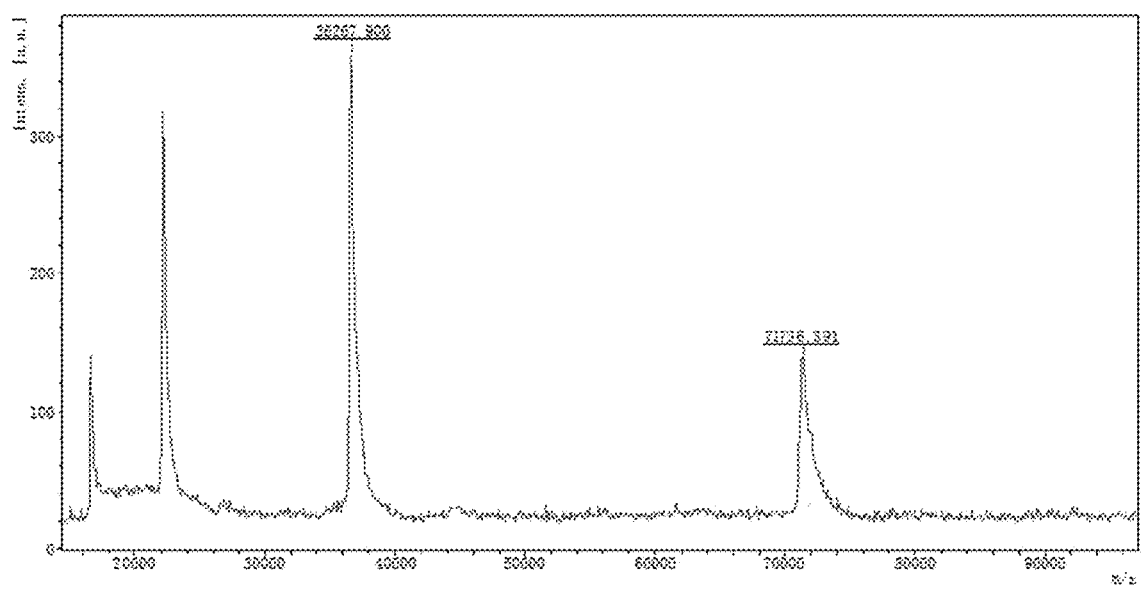
FIG. 1E shows molecular weight determination results of RHMH18 by matrix-assisted laser desorption/ionization time-of-flight mass spectrometry (MALDI-TOF-MS).

After the fermentation supernatant of the screened strain was subjected to WB verification, it was shown through results that His antigenicity, RGD antigenicity and HSA antigenicity were achieved at the same time, the protein of the fermentation supernatant was a fusion protein of Double linker, and the molecular size was 71796 Da, which was consistent with an expected one (FIG. 1E). A yeast genome was extracted, and it was shown through PCR amplification results that a target gene was in the yeast genome. It was shown through results that the strain obtained after screening was a strain expressing a target protein, and following researches were conducted with the screened strain as an original recombinant strain.

Example 3 Preparation and Purification of a Recombinant Protein

The screened strain was inoculated into a small shake flask and cultured at 28° C. and 200 rpm for 1 day to prepare a seed solution. The seed solution was inoculated into a 1 L triangular shake flask containing 300 mL of BMGY according to an inoculation amount of 2% (v/v). The seed solution was cultured at 28° C. and 200 rpm for 1 day and then subjected to standing overnight, and a fermentation supernatant was replaced with BMMY to induce protein secretion. 1% (v/v) of methanol was added every day, and after continuous culture at 28° C. and 150 rpm for 4 days, the fermentation supernatant was centrifuged at 8000 rpm for 10 minutes to obtain a required target protein.

Example 4 Expression and Purification of a Recombinant Protein

A fermentation solution was centrifuged at 8000 rpm for 10 minutes, and a fermentation supernatant was collected by centrifugation and filtered with a 0.45 μm filter membrane for sterilization. Then, the fermentation supernatant was subjected to ultrafiltration concentration 10 times by using an ultrafilter with a molecular weight cutoff of 10 kDa. An equal volume of water was added twice, and concentration was performed again. Blue Sepharose was first balanced with a solution A (20 mM NaPB pH 7.2, 0.1 M NaCl). After the fermentation supernatant obtained by centrifugation was filtered with the 0.45 μm filter membrane, the fermentation supernatant was loaded onto a Blue column, eluted with the solution A for balance, eluted with a 100% solution B (20 mM NaPB pH 7.2, 2 M NaCl) and then strongly washed with a solution C (1 M Arg, pH 7.2). A buffer solution was replaced with a solution D (25 mM Tris-HCl, 50 mM NaCl, 2 mM CaCl$_2$), pH 7.6) by using a G25 desalting column, and the solution was added into a dialysis bag with a molecular weight of 3000 for dialysis for 3 days, pre-frozen at −20° C. and then put into a freeze dryer for freeze-drying.

Example 5 Functional Verification of a Recombinant Protein

12% SDS-PAGE gel was prepared, and a fermentation supernatant was collected by centrifugation. After processing, a sample was loaded under electrophoresis condition of 150 V for 80 minutes and then transferred onto a nitrocellulose membrane. Three samples in a Marker range of 10 kDa-180 kDa were prepared, hybridized with an His monoclonal antibody, an RGD polyclonal antibody and an HSA polyclonal antibody respectively and then incubated with a goat anti-mouse secondary antibody. The incubated nitrocellulose membrane was subjected to color development with an ECL (chemiluminescent reagent) color developing solution. It was shown through results that all fusion proteins showed HSA specific bands, and the samples fused with RGD or His showed corresponding specific bands respectively, indicating that the albumin fusion proteins successfully expressed corresponding functional components (RGD, His).

Example 6 Morphology Analysis of Recombinant Nanoparticles

Morphological structures of recombinant fusion protein particles were observed by using a transmission electron microscope: A certain amount of the recombinant fusion protein particles in each group were added into an appropriate amount of an ultra-pure aqueous solution for ultrasonic full dispersion, and a suspension was sucked onto a copper screen mesh coated with a carbon membrane by using a pipette, naturally air-dried and then observed under a transmission electron microscope.

Figure 2:
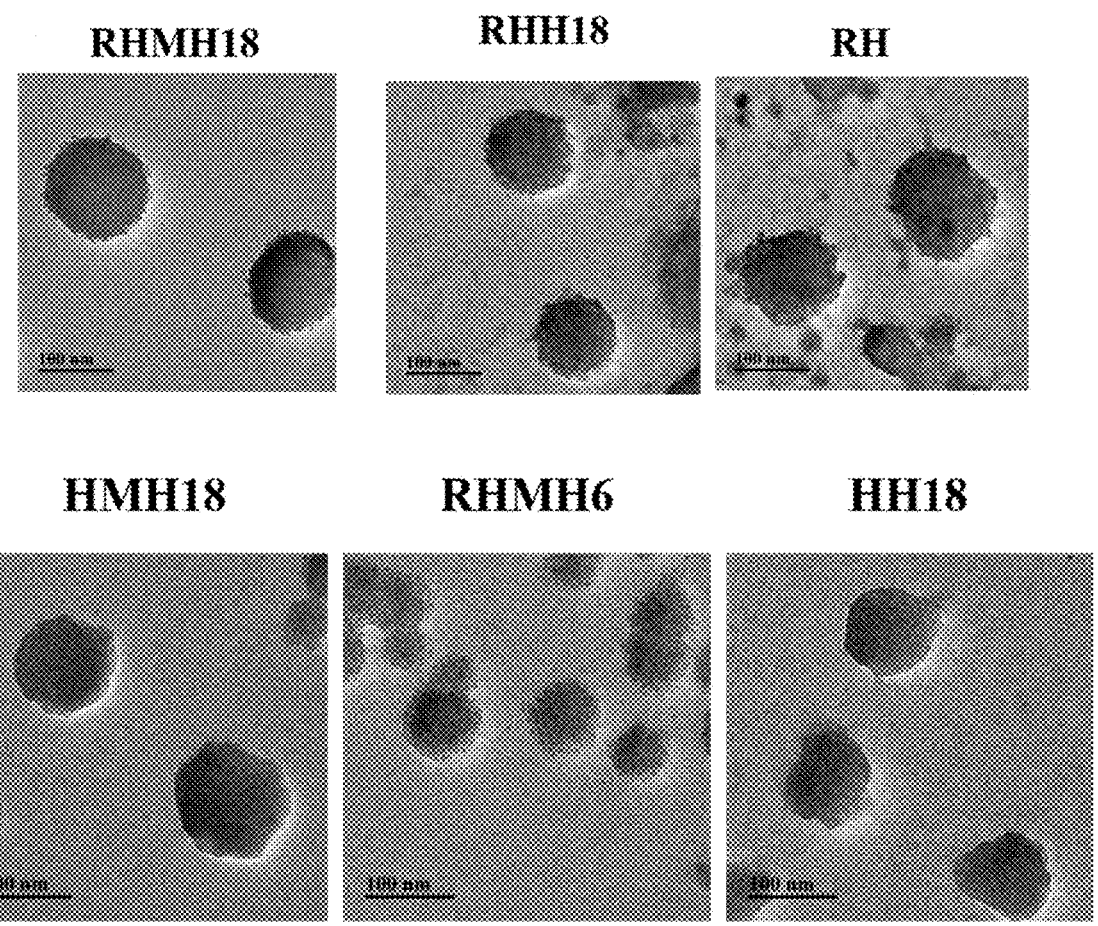
FIG. 2 shows transmission electron micrographs of various drug-loaded albumin fusion protein nanoparticles.
Figure 3A:
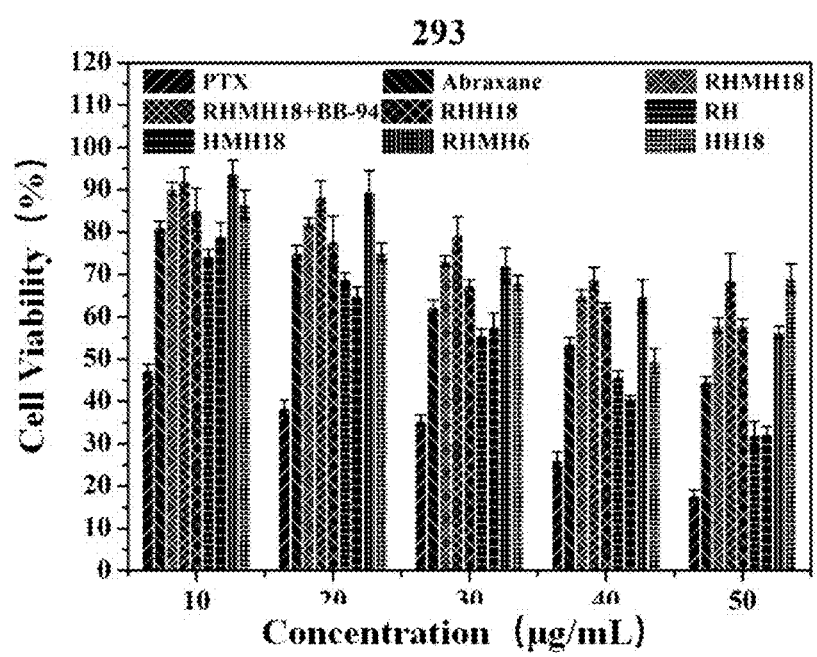
FIG. 3A shows test results of toxicity of various drug-loaded albumin fusion protein nanoparticles to a normal cell 293.
Figure 3B:
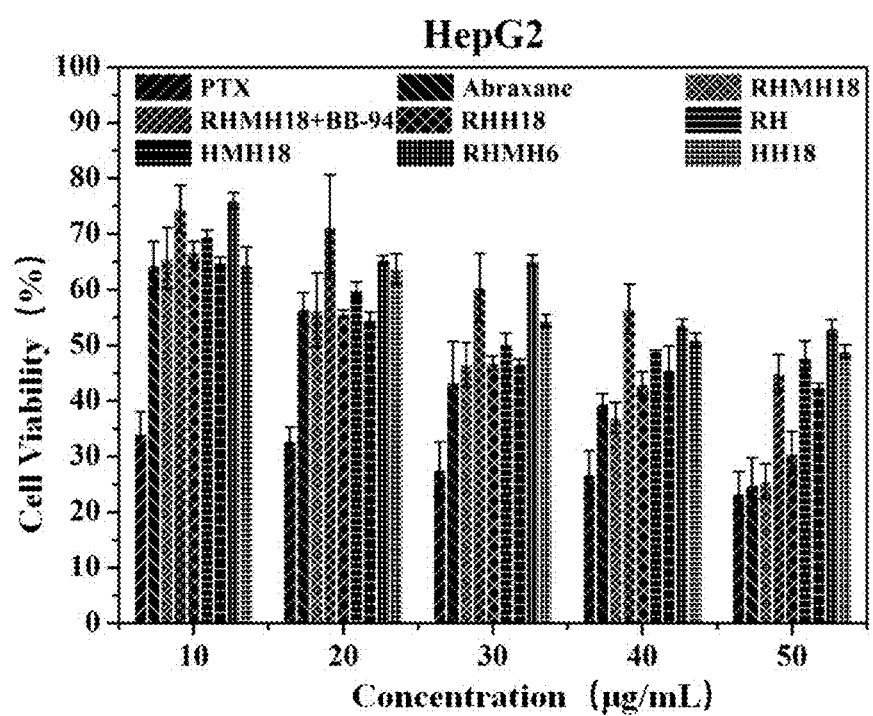
FIG. 3B shows test results of toxicity of various drug-loaded albumin fusion protein nanoparticles to a cancer cell HepG2.
Figure 3C:
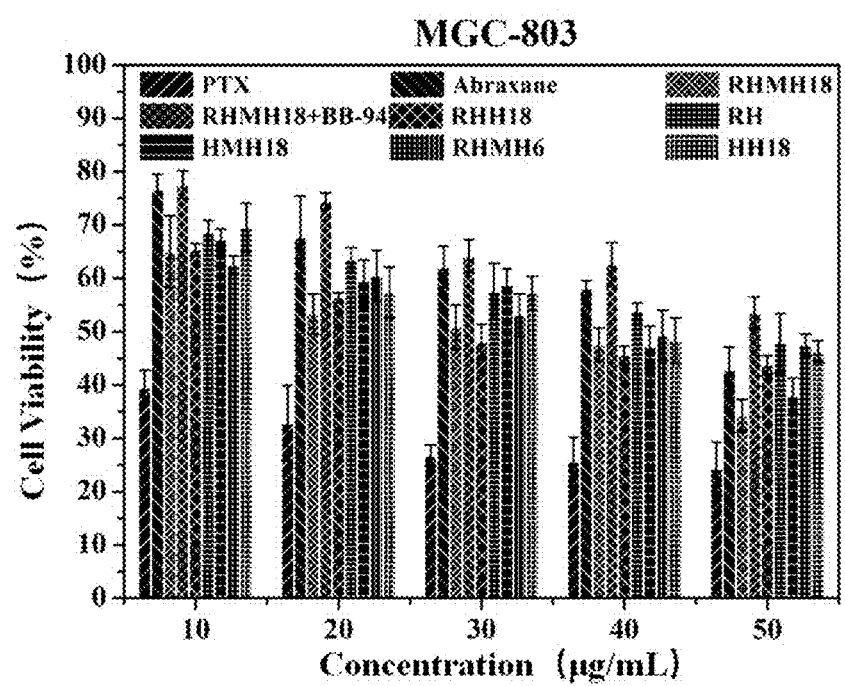
FIG. 3C shows test results of toxicity of various drug-loaded albumin fusion protein nanoparticles to a cancer cell MGC-803.
Figure 3D:
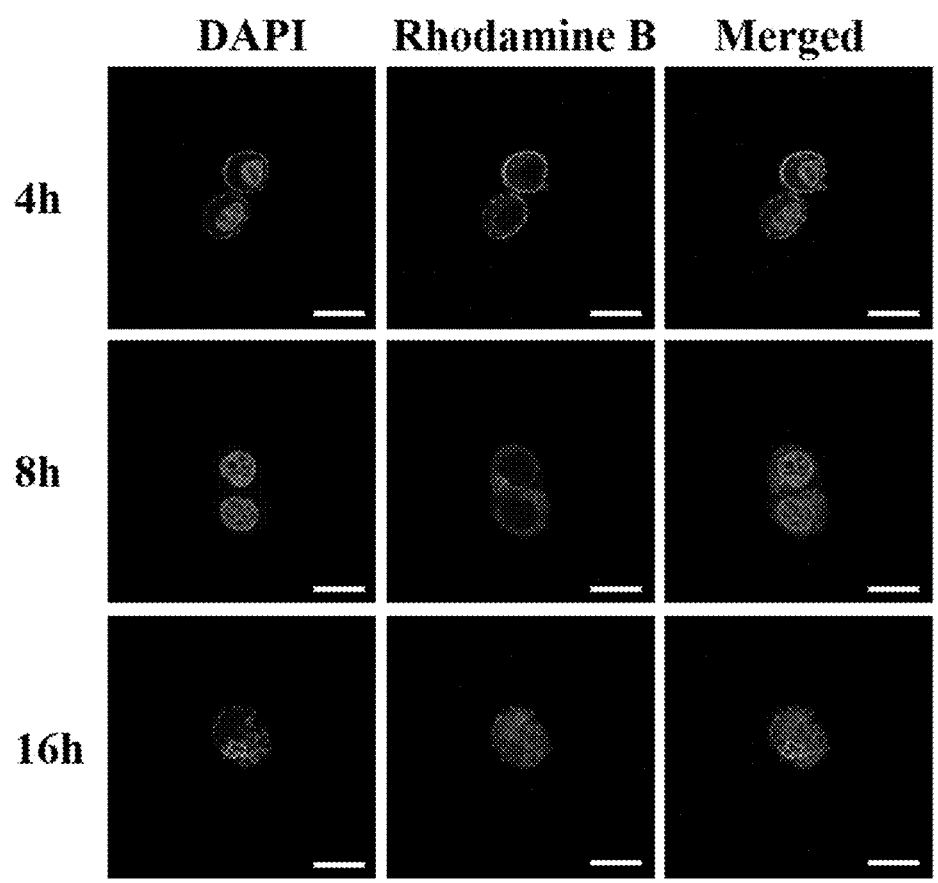
FIG. 3D shows uptake of a final nanoparticle (RHMH18) by the cancer cell HepG2.

As shown in FIG. 2, the formed recombinant protein nanoparticles were round with a diameter of 100 nm. The particles formed by RHMH18 were clear in appearance and uniform and regular in particle shape, and the smoothness of the appearance of other particles was lower than that of RHMH18.

Example 7 Loading of Paclitaxel with a Recombinant Fusion Protein

Albumin fusion protein powder freeze-dried by a freeze dryer was dissolved in a PBS buffer solution to prepare a 1 mg/ml solution, the pH was adjusted to 5.5 with a 1 mM HCl solution, after a 10 mg/mL paclitaxel solution was added, the pH was adjusted to 7.4 with a 1 mM NaOH solution, centrifugation was performed at 10000 rpm for 20 minutes, an obtained precipitate was uniformly mixed with ultrapure water and then centrifuged at 1000 rpm for 20 minutes, and the steps above were repeated 3 times to obtain a paclitaxel-loaded fusion protein nanoparticle. The drug loading rates of RHMH18, RHMH6, RHH18, HMH18, HH18 and RH were 6.59%, 3.21%, 5.88%, 5.64%, 5.09% and 6.38% respectively.

Example 8 Loading of Docetaxel with a Recombinant Fusion Protein

Albumin fusion protein powder freeze-dried by a freeze dryer was dissolved in a PBS buffer solution to prepare a 1 mg/mL solution, the pH was adjusted to 5.5 with a 1 mM HCl solution, after a 10 mg/ml docetaxel solution was added, the pH was adjusted to 7.4 with a 1 mM NaOH solution, centrifugation was performed at 10000 rpm for 20 minutes, an obtained precipitate was uniformly mixed with ultrapure water and then centrifuged at 1000 rpm for 20 minutes, and the steps above were repeated 3 times to obtain a fusion protein nanoparticle. The drug loading rates of RHMH18, RHMH6, RHH18, HMH18, HH18 and RH were 7.31%, 4.87%, 7.06%, 6.34%, 6.17% and 7.08% respectively.

Example 9 In-Vitro Drug Release of a Recombinant Fusion Protein

An appropriate amount of various nanoparticles were separately weighed and dissolved in corresponding PBS buffer solutions, mixed systems were transferred into a dialysis bag (3500 KD) with a mouth tightly tied with a cotton rope, the dialysis bag was placed in an EP tube containing 10 times volume of PBS and shaken in a constant-temperature shaker at 37° C. and 100 rpm, 3 mL of a release solution was separately sucked at 10 minutes, 20 minutes, 30 minutes, 1 hour, 2 hours, 3 hours, 5 hours, 7 hours, 9 hours, 11 hours, 24 hours, 27 hours and 48 hours, and 3 mL of a buffer solution with the same temperature and pH was added at the same time. The release solution labeled at each time point was collected, an absorption value was measured with an ultraviolet spectrophotometer, a cumulative release rate of PTX was calculated according to a standard curve, and then an in-vitro release curve of adriamycin was drawn based on the cumulative release rate versus time.

Example 10 Drug Toxicity Test of a Recombinant Fusion Protein

With the paclitaxel-loaded albumin fusion protein nanoparticle as an example: Three kinds of cells HEK 293, HepG2 and MGC-803 were cultured in a DMEM culture medium containing 10% of fetal bovine serum and 1% of a double antibody in an incubator containing 5% of $CO_2$ at 37° C., passage was performed once within 2 days, and the cells in a logarithmic growth phase was taken for an experiment.

The cells in the logarithmic growth phase were digested and counted and then inoculated into a 96-well plate at a density of $5*10^3$/well for culture. After cell attachment, a complete culture medium was changed into 100 μL of a recombinant protein solution with a drug concentration of 10 μg/mL, 20 μg/mL, 30 μg/mL, 40 μg/mL and 50 μg/mL respectively, the solution was sucked out after the cells were incubated for 24 hours, the cells were carefully rinsed with PBS three times to remove a material which has not been endocytosed by the cells, 100 μL of a 0.5 mg/mL MTT solution was added and then sucked out after the cells were continuously incubated in an incubator for 4 hours, DMSO was added for shaking for 15 minutes, and then the cells were detected on a microplate reader. A blank group without nanoparticles was used as a control. Each experiment was repeated three times to obtain an average value. It was shown through results that compared with free paclitaxel and protein nanoparticles (Abraxane, RH) without His fusion, other fusion protein samples showed better biocompatibility to normal cells, and the cell survival rate was above 70%; compared with commercially available Abraxane, paclitaxel-loaded RHMH18 showed stronger toxicity to a cancer cell HepG2, and when a particle concentration was 50 μg/mL, the cell survival rate was about 30%; paclitaxel-loaded RHMH18 showed cytotoxicity comparable to that of Abraxane to a cancer cell MGC-803, and when the particle concentration is 50 μg/mL, the cell survival rate was about 20%.

Example 11 Cellular Uptake of a Recombinant Fusion Protein

With the paclitaxel-loaded albumin fusion protein nanoparticle as an example: Cells HEK 293, HepG2, and MGC-803 in a logarithmic growth phase were separately inoculated into a 6-well plate at a density of $3*10^5$ cells/well. After cell attachment, a culture medium was changed into a culture medium solution (50 μg/mL) of a recombinant protein modified with rhodamine B, the solution was sucked out after the cells were incubated for 2 hours, and then the cells were carefully rinsed with PBS three times to remove a material which has not been endocytosed by the cells, digested with pancreatin, resuspended in PBS and quantitatively tested in a flow cytometer. It was shown through results that compared with other fusion protein nanoparticles, the three kinds of cells showed stronger uptake of RHMH18.

In addition, after cell attachment, the culture medium was changed into a culture medium solution of a recombinant protein with a drug concentration of 10 μg/mL, 20 μg/mL, 30 μg/mL, 40 μg/mL and 50 μg/mL respectively, the solution was sucked out after the cells were incubated for different time, and then the cells were carefully rinsed with PBS, digested with pancreatin, resuspended in PBS and tested in the flow cytometer. A blank group without protein particles was used as a control for adjustment. It was shown through apoptosis results that compared with other fusion protein nanoparticles, paclitaxel-loaded RHMH18 showed stronger killing ability to cancer cells.

HEK 293, HepG2 and MGC-803 were inoculated into a confocal cell culture dish at a density of $2*10^5$ cells/well, a culture medium solution containing a recombinant protein (400 mg/L) was added for co-incubation for a certain period of time, the cells were rinsed with PBS three times, a 4% paraformaldehyde solution was added for co-incubation for 20 minutes to fix the cells, then a 200 ng/ml DAPI solution was added for staining nuclei in an incubator for 30 minutes, and finally the cells were rinsed with PBS three times and qualitatively observed with a CLSM. With HepG2 as representative cells for analysis, it was shown through results that as culture time passed, RHMH18 crossed cell membranes and was gradually distributed in cytoplasm, and after culture for 16 hours, particles entered the nuclei to achieve a killing effect.

Comparative Example 1

A final drug loading rate was directly affected by a mixing ratio of albumin to a drug (for example, paclitaxel): Fusion albumin powder freeze-dried by a freeze dryer was dissolved in a PBS buffer solution to prepare a 1 mg/ml solution, the pH was adjusted to 5.5 with a 1 mM HCl solution, after a drug solution with a concentration of 5 mg/ml, 8 mg/ml, 12 mg/mL and 15 mg/ml was separately added, the pH was adjusted to 7.4 with a 1 mM NaOH solution, centrifugation was performed at 10000 rpm for 20 minutes, an obtained precipitate was uniformly mixed with ultrapure water and then centrifuged at 1000 rpm for 20 minutes, and the steps above were repeated 3 times to obtain a paclitaxel-loaded fusion protein nanoparticle. It was found after testing that compared with a drug concentration of 10 mg/ml, when the drug concentration is 5 mg/ml and 8 mg/ml, the drug loading efficiency of the nanoparticle is greatly reduced; when the drug concentration is 12 mg/mL and 15 mg/ml, the drug loading efficiency of the nanoparticle is comparable as that when the drug concentration is 10 mg/mL.

Comparative Example 2

A final drug loading rate was directly affected by the pH when albumin and a drug (for example, paclitaxel) was mixed: Fusion albumin powder freeze-dried by a freeze dryer was dissolved in a PBS buffer solution to prepare a 1 mg/ml solution, the pH was separately adjusted to 7, 6.5, 6 and 5 with a 1 mM HCl solution, after a drug solution with a concentration of 10 mg/ml was added, the pH was adjusted to 7.4 with a 1 mM NaOH solution, centrifugation was performed at 10000 rpm for 20 minutes, an obtained precipitate was uniformly mixed with ultrapure water and then centrifuged at 1000 rpm for 20 minutes, and the steps above were repeated 3 times to obtain a paclitaxel-loaded fusion protein nanoparticle. It was found after testing that the drug loading rate of RHMH18 was separately 2.35%, 4.14%, 5.21% and 5.19%.

Although the disclosure has been disclosed as above in preferred examples, the examples are not intended to limit the disclosure. Various changes and modifications can be made by anyone familiar with this technology without departing from the spirit and scope of the disclosure. Therefore, the protection scope of the disclosure should be defined by the claims.

---

What is claimed is:

1. A fusion protein, wherein the amino acid sequence of the fusion protein is as set forth in SEQ ID NO: 1.

2. A microbial cell, expressing the fusion protein according to claim 1.

3. The microbial cell according to claim 2, comprising a bacterial cell or a fungal cell.

4. The microbial cell according to claim 3, wherein the cell is a yeast cell, comprising *Pichia pastoris* and *Saccharomyces cerevisiae*.

5. The microbial cell according to claim 4, wherein the yeast is *Pichia pastoris* SMD1168H.

6. The microbial cell according to claim 4, wherein the yeast is *Pichia pastoris* SMD1168H, which expresses the fusion albumin as set forth in SEQ ID NO: 1 with pPICZαA as an expression vector.

7. The microbial cell according to claim 4, wherein the gene encoding the fusion protein according to claim 1 is fused into a genome.

8. A controlled release type pharmaceutical composition, wherein the fusion albumin according to claim 1 is used as a carrier for drug loading.

9. The pharmaceutical composition according to claim 8, wherein a drug or siRNA is loaded by using a pH response self-assembly technology, and the drug comprises paclitaxel, docetaxel and adriamycin.

10. The pharmaceutical composition according to claim 8, wherein the pharmaceutical composition is obtained by mixing the fusion albumin and the drug in a ratio of 1:2-10 at a pH of 5-6 and then performing self-assembly at a pH adjusted to 7-8.

11. The pharmaceutical composition according to claim 8, wherein the drug is used to prevent or treat at least one disease of liver cancer, gastric cancer, lung cancer, breast cancer or cervical cancer.

12. The pharmaceutical composition according to claim 8, wherein the drug is a tumor cell inhibitor.

13. The pharmaceutical composition according to claim 8, wherein a tumor cell comprises HepG2, MGC-803, A549, MCF-7 or HeLa.

\* \* \* \* \*